United States Patent [19]

Mahmood

[11] Patent Number: 4,929,608

[45] Date of Patent: May 29, 1990

[54] EMULSIFIABLE CONCENTRATES OF MALATHION

[75] Inventor: Tario Mahmood, Flanders, N.J.

[73] Assignee: American Cyanamid Company, Stamford, Conn.

[21] Appl. No.: 729,723

[22] Filed: May 2, 1985

[51] Int. Cl.$^5$ ............................................ A01N 57/00
[52] U.S. Cl. .................................... 514/122; 514/975
[58] Field of Search ............................. 514/122, 975

[56] References Cited

U.S. PATENT DOCUMENTS

| | | | |
|---|---|---|---|
| 3,030,264 | 4/1962 | Baker et al. | 514/122 |
| 3,396,223 | 8/1968 | Stark, Jr. | 514/122 |
| 3,515,782 | 11/1964 | Nolan | 514/122 |
| 3,683,078 | 8/1972 | Haus | 514/122 |
| 3,777,024 | 12/1973 | Martin et al. | 514/122 |
| 3,961,043 | 6/1976 | Huvar | 514/122 |

OTHER PUBLICATIONS

McCutcheon's, Emulsifiers and Detergent, (1982), North American Edition, p. 134.

*Primary Examiner*—Allen J. Robinson
*Attorney, Agent, or Firm*—Estelle J. Tsevdos

[57] ABSTRACT

The present invention relates to emulsifiable concentrate compositions of phosphorodithioates, especially [S-1,2-bis-(ethoxycarbonyl)ethyl] O,O-dimethylphosphorodithioate, known as malathion insecticide, containing vegetable oils as the solvent. These compositions not only form stable such emulsions but are even stable when diluted with water.

8 Claims, 1 Drawing Sheet

EMULSIFIABLE CONCENTRATES OF MALATHION

BACKGROUND OF THE INVENTION

The phosphorodithioates are well-known and valuable insecticides especially useful for the control of aphids, mosquitoes, Mediterranean fruit flies and a variety of other outdoor and household insects. One such phosphorodithioate, [S-1,2-bis-(ethoxycarbonyl)ethyl]0,0-dimethylphosphorodithioate, known as malathion (hereinafter referred to as malathion), is disclosed in U.S. Pat. No. 2,578,652, issued to Cassady on Dec. 18, 1951, incorporated herein by reference. This malathion insecticide can be processed in a variety of ways, one of which subjects the malathion to the action of a nonreactive gas containing ozone. This process reduces the objectionable odor of phosphorodithioates, such as malathion, and is disclosed in U.S. Pat. No. 2,980,723, issued to Frank and Gagliardi on Apr. 18, 1961, incorporated herein by reference.

Technical grade insecticidal formulations of malathion are disclosed in U.S. Pat. No. 3,396,223 issued to Stark on Aug. 6, 1968 and U.S. Pat. No. 3,515,782 issued to Nolan on June 2, 1970. However, other formulations of malathion useful in controlling insect pests have been developed. One such composition effective for aerial distribution and for Low Volume (LV) application containing a phosphorodithioate, also contains a specific phenoxyacetic acid ether herbicide and an aromatic diluent additive defined by aromatic contents, mixed aniline point, specific gravity and evaporation rate (U.S. Pat. No. 3,352,664 issued to Nolan et al on Nov. 14, 1967, incorporated herein by reference).

As such, malathion insecticidal formulations are available in several commercial forms, but the emulsifiable concentrate form is preferable for ease of application. Typical emulsifiable concentrate formulations comprise, on a weight bases, about 30% to 70% malathion insecticide, about 3% to 10% of a surfactant or surfactants blend and the remaining portion being an enert aromatic solvent, such as xylene or a heavy aromatic solvent, such as xylene or a heavy aromatic naphtha. Recently, however, the inclusion of these aromatic solvents has come under disfavor due to environmental concerns. Therefore, emulsifiable concentrate formulations excluding such aromatics have been and continue to be sought.

SUMMARY OF THE INVENTION

The present invention relates to emulsifiable concentrate compositions containing malathion insecticide utilizing solvents which are environmentally acceptable, such as vegetable oils. It has been unexpectedly discovered that phosphorodithioates, such as malathion, containing a vegetable oil as solvent are readily applicable for use in Low Volume (LV) and Ultra Low Volume (ULV) application techniques and that such emulsions are stable even when diluted with water for aqueous application.

It is an object of the present invention, therefore, to provide stable emulsifiable concentrate compositions containing malathion in a vegetable oil solvent.

It is another object of this invention to provide stable yet effective vegetable-oil malathion compositions which are not only directly applied by utilizing standard Low Volume (LV) and Ultra Low Volume (ULV) application techniques but also are stable when diluted with water to form aqueous-based compositions for application.

These and further objects of the present invention will become more apparent by the following more detailed description of the invention.

DESCRIPTION OF DRAWINGS

FIG. I: Characteristic Infrared absorption spectrum of Flo Mo 1002 ® surfactant blend sold by DeSoto, Inc., Sellers Chemical Division.

DESCRIPTION OF THE INVENTION

Figure 1:
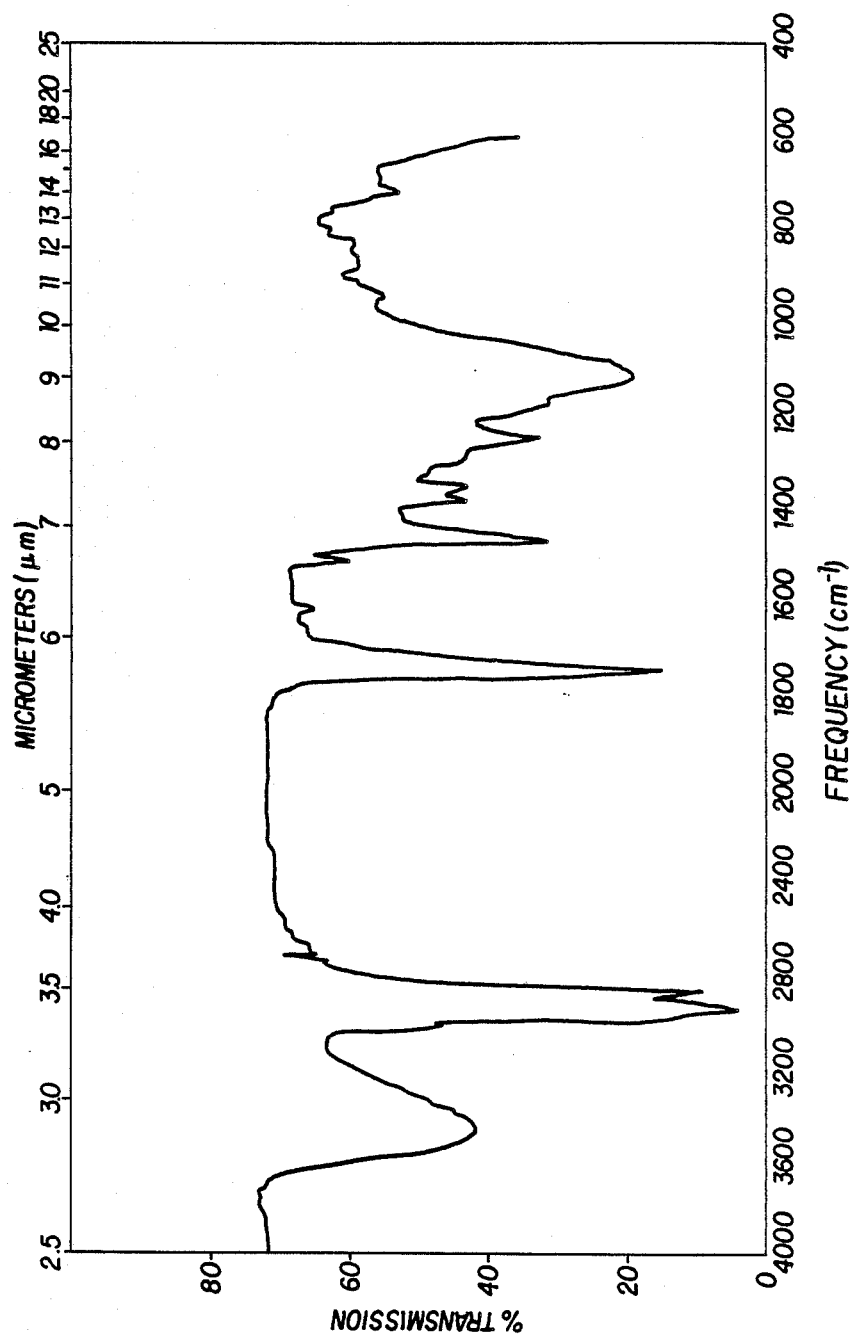

The present invention relates to emulsifiable concentrate compositions comprising, on a weight basis, 10.0% to 55.0% phosphorodithioate such as [S-1,12-bis-(ethoxycarbonyl)ethyl] 0,0-dimethylphosphorodithioate (malathion); 8.0% to 15.0% of the surfactant known under the trademark of Flo Mo 1002 ® surfactant; up to 5.0% (0.001% to 5.0%) of a calcium alkyl aryl sulfonate; and vegetable oil to total the composition of 100.0%.

Other phosphorodithioate insecticides also may be formulated into the compositions of the present invention.

Flo Mo 1002 ® surfactant is a proprietary surfactant blend sold by DeSoto, Inc., Sellers Chemical Division. It contains a blend of ethoxylated nonionic surfactants having a specific gravity of 0.971, a boiling point of 300° F., a percent volatiles, by volume, of 8.0% and is indentified by the Infrared Spectrum indicated in FIG. I. Surprisingly, this particular surfactant blend results in emulsifiable concentrate compositions of malathion insecticide in vegetable oil solvents which have acceptable emulsion stability in water, as compared to a variety of commercially-available ethoxylated surfactant blends. The emulsifiable concentrate compositions of the invention thus provide vegetable oil-based formulations of malathion which are unique in their suitability for use both by direct application and in aqueous systems.

The vegetable oils useful as solvents in the present invention include cottonseed oil, soybean oil, corn oil or mixtures thereof, as well as other such vegetable oils known to those skilled in the art. Cottonseed oil is preferred in the compositions of the present invention.

Additionally, calcium alkyl aryl sulfonates in amounts up to 5.0%, by weight, (0.001% to 5.0%), preferably up to 2.0% (0.001% to 2.0%) are useful in the compositions of the present invention. Calcium dodecylbenzene sulfonate is an example of such a surfactant.

The compositions of this invention may be readily prepared by admixing, on a weight basis, about 10.0% to 55.0% malathion with about 8.0% to 15.0% Flo Mo 1002 ® surfactant and up to 5.0% calcium alkyl aryl sulfonate surfactant. Then, the vegetable oil is added to the stirred homogeneous mixture to total to 100%, and mixing is continued until a clear solution is obtained. The temperature during this mixing is maintained at about 25° C. to 40° C., but the resulting composition then is cooled to ambient temperatures and packaged in suitable containers.

The following examples are provided to further illustrate the compositions of the present invention but are not limitative of the invention described herein.

EXAMPLE 1

Preparation of emulsifiable concentrates of malathion insecticide for emulsion stability studies Malathion insecticide and one or more emulsifiers (totalling 10% by weight) are mixed with cottonseed oil. The mixture is then stirred and heated, if necessary, until a homogeneous solution forms. The percent by weight of components of the emulsifiable concentrates prepared in this manner is given in Table I.

Emulsion Stability Tests

Standard hard water is prepared by dissolving anhydrous calcium chloride (0.304 g) and magnesium chloride hexahydrate (0.13 g) in distilled water. The volume is adjusted to one liter to yield water with a hardness value of 342 ppm calcium carbonate.

Standard hard water (75 to 80 mL) is added to a Standard 100 mL graduated cylinder. The emulsifiable concentrate is added via a pipette, with the flow of the concentrate being directed towards the center of the cylinder. The volume is adjusted to 100 mL with standard hard water; the cylinder is inverted 15 times and then is allowed to stand at room temperature for one hour before it is examined for any creaming or separation. In this context, creaming is defined as a layer of the formulation located at the top or bottom of the emulsion, containing a proportion of the dispersed phase greater than that contained in the remainder of the emulsion. An emulsion prepared from 5 mL concentrate and 95 mL standard hard water is regarded as acceptable if any separation, including creaming at the top and sedimentation at the bottom, does not exceed 3 mL. The results of these tests, which were conducted on the compositions prepared by the above procedure, are summarized in Table I.

What is claimed is:

1. Emulsifiable concentrate compositions comprising, on a weight basis: 10.0% to 55.0% [S-1,2-bis-(ethoxycarbonyl) ethyl] 0,0-dimethyl phosphorodithioate (malathion); 8.0% to 15.0% the ethoxylated nonionic surfactant blend having a boiling point of 300° F., a specific gravity of 0.971, a percent volatiles by volume of 8.0% and identified by the Infrared Spectrum indicated in FIG. I; and a vegetable oil to total said composition to 100.0%.

2. A composition according to claim 1, wherein said vegetable oil is cottonseed oil, soybean oil, corn oil or mixtures thereof.

3. A composition according to claim 2, wherein said vegetable oil is cottonseed oil.

4. A composition according to claim 3, wherein said composition comprises, on a weight basis: 45.0% to 55.0% [S-1,2-bis-(ethoxycarbonyl) ethyl] 0,0-dimethyl phosphorodithioate; 10.0% ethoxylated nonionic surfactant blend known under the tradename of Flo Mo 1002 ® surfactant; and cottonseed oil.

5. Emulsifiable concentrate compositions comprising, on a weight basis: 10.0% to 55.0% [s-1,2-bis-(ethoxycarbonyl) ethyl]-0,0-dimethyl phosphorodithioate (malathion; 8.0% to 15.0% of the ethoxylated nonionic surfactant blend having a boiling point of 300° F., a specific gravity of 0.971, a percent volatiles by volume of 8.0% and identified by the Infrared Spectrum indicated in FIG. I 0.001% to 5.0% calcium dodecylbenzene sulfonate; and a vegetable oil to total said composition to 100.0%.

6. A composition according to claim 5 wherein said vegetable oil is cottonseed oil, soybean oil, corn oil or mixtures thereof.

7. A composition according to claim 6, wherein said vegetable oil is cottonseed oil.

TABLE I

| Formulation No | Malathion % | Cotton seed oil % | Surfactant 10% | Emulsion test Creaming one hr | Comment |
|---|---|---|---|---|---|
| 1 Invention | 53.0 | 37.0 | [1]Flo Mo 1002 ® | <3 mL | acceptable |
| 2 Invention | 53.0 | 37.0 | [1]Flo Mo 1002 ® 8% + Calcium dodecylbenzene sulfonate (50) 2% | <3 mL | acceptable |
| 3 | 53.0 | 37.0 | [2]Trylox CO 30 ® (Ethoxylated castor oil 30 mol EO) | >6 mL | Not acceptable |
| 4 | 53.0 | 37.0 | [2]Trylox CO 36 ® (Ethoxylated castor oil 36 mol EO) | >6 mL | Not acceptable |
| 5 | 53.0 | 37.0 | [1]Flo Mo 1093 ® (Blend of nonionic surfactants) | >6 mL | Not acceptable |
| 6 | 53.0 | 37.0 | [3]Triton N101 ® (Nonylphenol 10 mol EO) | >10 mL | Not acceptable |
| 7 | 53.0 | 37.0 | [4]Igepon DM 710 ® (Dinonylphenol 10 mol EO) | >10 mL | Not acceptable |

[1]Trademark DeSoto, Inc
[2]Trademark Rohm and Haas Co.
[3]Trademark Emery Ind.
[4]Trademark GAF Corp.

The results summarized in Table I demonstrate the superior aqueous emulsion stability of the compositions of the present invention when compared to other emulsifiable concentrate malathion insecticide compositions employing a variety of commercially-available ethoxylated surfactants.

8. A composition according to claim 7, wherein said composition comprises, on a weight basis: 45.0% to 55.0% [S-1,2-bis-(ethoxycarbonyl)ethyl]-0,0-dimethyldphosphoroithioate (malathion); said nonionic surfactant blend 0.001% to 2.0% calcium dodecylbenzene sulfonate; and 33.0% to 47.0% cottonseed oil.

* * * * *